(12) United States Patent
Akutagawa et al.

(10) Patent No.: US 10,300,021 B2
(45) Date of Patent: May 28, 2019

(54) INTRAORALLY RAPIDLY DISINTEGRATING TABLET

(75) Inventors: Tomoya Akutagawa, Iwakuni (JP); Masahiko Narasaki, Iwakuni (JP)

(73) Assignee: Teijin Pharma Limited, Chiyoda-ku, Tokyo (JP)

( * ) Notice: Subject to any disclaimer, the term of this patent is extended or adjusted under 35 U.S.C. 154(b) by 0 days.

(21) Appl. No.: 12/092,852

(22) PCT Filed: Nov. 14, 2006

(86) PCT No.: PCT/JP2006/323061
§ 371 (c)(1),
(2), (4) Date: May 7, 2008

(87) PCT Pub. No.: WO2007/055427
PCT Pub. Date: May 18, 2007

(65) Prior Publication Data
US 2009/0117182 A1    May 7, 2009

(30) Foreign Application Priority Data

Nov. 14, 2005    (JP) .................... 2005-328722

(51) Int. Cl.
| | |
|---|---|
| A61K 9/50 | (2006.01) |
| A61K 9/16 | (2006.01) |
| A61K 9/00 | (2006.01) |
| A61K 31/131 | (2006.01) |
| A61K 31/137 | (2006.01) |
| A61K 31/375 | (2006.01) |
| A61K 31/426 | (2006.01) |

(52) U.S. Cl.
CPC .......... *A61K 9/5026* (2013.01); *A61K 9/0056* (2013.01); *A61K 31/131* (2013.01); *A61K 31/137* (2013.01); *A61K 31/375* (2013.01); *A61K 31/426* (2013.01); *A61K 9/1635* (2013.01)

(58) Field of Classification Search
CPC .......................... A61K 9/5026; A61K 9/0056
USPC ........................................ 424/464
See application file for complete search history.

(56) References Cited

U.S. PATENT DOCUMENTS

| | | | | |
|---|---|---|---|---|
| 4,684,516 A | * | 8/1987 | Bhutani ................ | 424/469 |
| 6,287,596 B1 | * | 9/2001 | Murakami et al. ............ | 424/464 |
| 6,660,382 B2 | * | 12/2003 | Nouri et al. ................. | 428/403 |
| 2002/0098227 A1 | | 7/2002 | Nouri et al. | |
| 2003/0049315 A1 | | 3/2003 | Daggy et al. | |
| 2003/0215500 A1 | | 11/2003 | Ohta et al. | |
| 2004/0122106 A1 | * | 6/2004 | Ohta et al. .................... | 514/630 |
| 2004/0265380 A1 | * | 12/2004 | Delmas et al. ............... | 424/466 |
| 2005/0112196 A1 | | 5/2005 | Xie et al. | |
| 2006/0078614 A1 | * | 4/2006 | Venkatesh ............ | A61K 9/0056 424/469 |
| 2006/0134199 A1 | | 6/2006 | Suga et al. | |

FOREIGN PATENT DOCUMENTS

| | | |
|---|---|---|
| CA | 2375600 A1 | 1/2001 |
| CN | 1373658 A | 10/2002 |
| EP | 1595533 A1 | 11/2005 |
| FR | 2795962 A1 | 1/2001 |
| JP | 5-271054 | 10/1993 |
| JP | 2000344660 A | 12/2000 |
| JP | 2003-504324 A | 2/2003 |
| JP | 2005-112561 A | 4/2005 |
| JP | 2005-112861 A | 4/2005 |
| JP | 2007-153887 A | 6/2007 |
| JP | 4934144 B2 | 5/2012 |
| JP | 5123517 B2 | 1/2013 |
| WO | 02/02083 A1 | 1/2002 |
| WO | 2004/064810 A1 | 8/2004 |
| WO | 2004/075828 A2 | 9/2004 |
| WO | 2005/034921 A1 | 4/2005 |
| WO | 2008/122993 A1 | 10/2008 |

OTHER PUBLICATIONS

Becker, Febuxostat Compared with Allopurinol in Patients with Hyperuricemia and Gout, The New England Journal of Medicine, vol. 353, No. 23, 2005.*
Chinese Office Action issued in corresponding to Patent Application No. 200680042409.3, dated May 28, 2010.
Office Action issued in corresponding Canadian Patent Application No. 2,629,487 dated Aug. 20, 2012 (in the name of Teijin Pharma Limited).
Australian Office Action dated Jun. 1, 2011, in corresponding Australian Patent Application No. 2006312566 (in the name of Teijin Pharma Limited).
European Extended Search Report dated Jun. 9, 2011, in corresponding European Patent Application No. 06823462.4 (in the name of Teijin Pharma Limited).
Office Action dated Jul. 3, 2012, in corresponding Japanese Patent Application No. 2006-307914.
Office Action issued in corresponding Taiwan Patent Application No. 095142089 dated Feb. 24, 2012.
Office Action issued in corresponding Canadian Patent Application No. 2,629,487 dated May 8, 2013.
Office Action for Indian Application No. 4110/DELNP/2008, dated Aug. 8, 2013.
Office Action for Chinese Patent Application No. 201310682491.8 dated Nov. 26, 2014.

\* cited by examiner

*Primary Examiner* — Adam C Milligan
(74) *Attorney, Agent, or Firm* — Sughrue Mion, PLLC

(57) ABSTRACT

The present invention provides an intraorally rapidly disintegrating tablet that can be formed using an ordinary apparatus, that has hardness with no practical problem and that disintegrates rapidly with good feeling in the oral cavity.

The present invention is intraorally rapidly disintegrating tablet produced by compression molding of a granule coated with a disintegrant, in which the granule contains a disintegrant also inside thereof and a drug except ambroxol hydrochloride inside and/or outside thereof.

10 Claims, No Drawings

INTRAORALLY RAPIDLY DISINTEGRATING TABLET

CROSS REFERENCE TO RELATED APPLICATIONS

This application is a National Stage of International Application No. PCT/JP2006/323061 filed on Nov. 14, 2006, claiming priority based on Japan Patent Application No. 2005-328722, filed Nov. 14, 2005, the contents of all of which are incorporated herein by reference in their entirety.

TECHNICAL FIELD

The present invention relates to an intraorally rapidly disintegrating tablet. More particularly, the present invention relates to an intraorally rapidly disintegrating tablet can be formed using an ordinary apparatus, has hardness with no practical problem and disintegrates rapidly with good feeling in the oral cavity.

BACKGROUND ART

Intraorally rapidly disintegrating tablets disintegrate rapidly in the oral cavity and attract attention as a dosage form to improve easiness of taking drugs and increase patients' compliance. Various types of intraorally rapidly disintegrating tablets have been invented. Intraorally rapidly disintegrating tablets frequently contain sugar alcohol such as mannitol as an excipient, taking rapid dissolution in the oral cavity into consideration. However, sugar alcohol is a major cause of troubles in tableting (such as sticking) during tablet formation and thus deteriorates compression moldability, and therefore sometimes makes it difficult to secure hardness that is of no practical problem. Accordingly, a technique of tableting in which an appropriate amount of water is contained during manufacturing has been disclosed (See, for example, Japanese Patent Application Laid-open No. H5-271054). This technique generally requires a particular apparatus, however, and furthermore tableting is conducted under a low level of compression, resulting in a limited hardness. Also, a technique in which fine sugar alcohol with an average particle size of 30 μm or less is used to perform tableting to form tablets under a dry condition (See US Patent Application Publication No. 2003/0215500) has been disclosed. This technique also uses sugar alcohol as a major ingredient. Therefore, in order to prevent the above-described troubles in tableting, an increase in the amount of a lubricant and limitation of pressure at tableting are inevitably required. As a result, intraorally rapidly disintegrating property and hardness were restricted. Further, although a technique in which a binder such as cellulose is added (See, for example, US Patent Application Publication No. 2003/0049315) has been proposed, addition of a binder poses problems such as deterioration of feeling in the mouth during disintegration of a tablet in the oral cavity. Furthermore, although a technique in which a granule containing sugar alcohol that is coated with a disintegrant are subjected to tableting to form tablets (See International Publication No. WO 2004/064810) has been proposed, the technique has such a problem that an intraoral disintegration time is long. In addition, US Patent Application Publication No. 2005/0112196 discloses a tablet comprising a granule containing a disintegrant both inside and outside thereof. Since a granule is not coated with the disintegrant, however, distribution of the disintegrant differs from that of the tablet of the present invention and the advantage of the present invention is not exerted.

DISCLOSURE OF INVENTION

An object of the present invention is to provide an intraorally rapidly disintegrating tablet can be formed using an ordinary apparatus, has hardness with no practical problem and disintegrates rapidly with good feeling in the oral cavity.

The present inventors found that if a tablet is composed of a granule that comprises a disintegrant inside thereof and coated with a disintegrant, an ordinary apparatus can be used to form a tablet which has hardness with no practical problem and disintegrates rapidly with good feeling in the oral cavity.

In other words, the present invention is an intraorally rapidly disintegrating tablet produced by compression molding of a granule coated with a disintegrant, wherein the granule comprises a disintegrant also inside thereof and a drug inside and/or outside thereof.

The present invention can be also expressed as an oral fast disintegrating tablet produced by compression molding of a granule which is prepared from powder comprising at least a disintegrant and then is coated with a disintegrant, in which a drug is added during the granule preparation and/or during the compression molding.

The present invention is also a granule used for tablet forming, wherein the granule comprises a disintegrant inside thereof, may further comprise a drug, and is coated with a disintegrant.

The tablet according to the present invention can be formed using an ordinary apparatus, has hardness with no practical problem and disintegrates rapidly with good feeling in the oral cavity.

BEST MODE FOR CARRYING OUT THE INVENTION

The drug used in the tablet of the present invention is not particularly limited, as far as it does not have properties that cause particular troubles in manufacturing of the tablet of the present invention by an ordinary manufacturing method, but excluded ambroxol or pharmaceutically acceptable salt thereof. Examples of the drug can include one or two or more kinds of active ingredients selected from central nervous system drugs, peripheral nervous system drugs, cardiovascular drugs, digestive organ drugs, hormone preparations, urogenital organ drugs, blood and body fluid drugs, metabolism drugs, antigout preparations, antineoplastics, antiallergic drugs, bronchodilators, antibiotics, antimicrobial drugs, antiviral drugs, wound care drugs, anticonvulsants, anticholinergic drugs, antihistamic drugs, antiinflammatory drugs, anticholesterol drugs, antilipids, anorexiants, stimulants, coagulants, antacids, chemotherapeutic drugs, nutritional supplements, diagnostics, narcotics and antihypnotic drugs, analgesics, cough suppressants, expectorants and the like.

More specific examples can include one or two or more kinds of active ingredients selected from the group consisting of, for example, ascorbic acid, acetaminophen, ethenzamide, alendronate, febuxostat, clenbuterol hydrochloride, ethyl icosapentate, tacalcitol, picosulfate, alfacalcidol, a compound described in International Publication No. WO99/26918, a compound described in International Publication No. WO 01/53291, and a compound described in International Publication No. WO 99/25686 and salts thereof, and hydrates of these compounds and salts thereof.

According to the tablet of the present invention, the drug is contained at least in either the inside of the granule constituting the tablet or the outside of the granule coated with a disintegrant. It is preferable, however, that the drug is contained only in the outside of the granule to secure rapid disintegration.

The drug used in the tablet of the present invention may be coated with a film-coating agent, an excipient, a binder, a lubricant, or the like depending on its properties, and a plasticizer may be added.

The disintegrant used in the tablet of the present invention is not particularly limited, as far as it is a disintegrant used for pharmaceutical preparations. Examples can include crospovidone, crystalline cellulose, hydroxypropylcellulose with a low degree of substitution, croscarmellose sodium, carmellose calcium, carboxystarch sodium, carboxymethyl starch sodium, potato starch, wheat starch, corn starch, rice starch, partly pregelatinized starch, and hydroxypropyl starch. One or two or more of these can be used. Crospovidone is particularly preferable. The sort of disintegrant used for coating granules according to the present invention may be identical to or different from that used inside the granules.

The disintegrant must be present both in the inside of the granule and in a coating on the granule constituting the tablet of the present invention. When the disintegrant is present only either in the inside of the granule or in a coating on the granule, sufficient intraorally rapidly disintegrating property is not achieved. Intraorally rapidly disintegrating property refers to a property of disintegrating within 1 minute to 30 seconds in the oral cavity. However, intraorally rapidly disintegrating property appropriate for a purpose is sufficient and not necessary to adhere to the absolute value.

Coating with a disintegrant also contributes to improvement of compression moldability. That is to say, the presence of a disintegrant both in the inside of the granule and in a coating on a granule is required for good compression moldability.

When a disintegrant is present in the "inside" of a granule, the possibility that the disintegrant is also present in a part close to the surface of the granule is not excluded. It is preferable from a viewpoint of securing rapidly disintegrating property that a disintegrant present in the inside of a granule is evenly dispersed in the granule together with other components of the granule. Furthermore, the disintegrant may be added in the outside of a granule in addition to the inside of a granule and the coating on the granule.

It is sufficient that the disintegrant used in the present invention is present in the inside of or in a coating on a granule as described above, and the amount of the disintegrant is not particularly limited. However, when the amount of the disintegrant in the inside of and in the coating on a granule is excessively large, feeling in the mouth, texture, disintegrating property, and compression moldability deteriorate, and when the amount is excessively small, disintegrating property and/or compression moldability deteriorate.

A preferable content of the disintegrant is influenced by sort of the drug, by sort of a disintegrant used, by sort of an additive, if the tablet contains an additive such as an excipient or a binder described below, their particle size, the materials of a manufacturing apparatus, and the like, but in general, the proportion of the disintegrant contained in the inside of a granule accounts for 4 to 20% by weight of a whole tablet, and the proportion of the disintegrant contained in the coating on a granule accounts for 4 to 20% by weight of a whole tablet.

When the amount exceeds the range, it is considered probable from the viewpoint of disintegrating property that the surface of a tablet or a granule is completely coated with a disintegrant and thereby water-conducting mechanism becomes insufficient to deteriorate the disintegrating property. When an excipient described below is used together, however, the upper limit may be influenced by the type and particle size of the excipient contained in the inside of the granule. For example, when the excipient in the inside of a granule is erythritol with an average particle size of about 20 µm, the disintegrating property may sometimes become poor when the proportion of the disintegrant in the coating on a granule and in the inside of the granule exceeds 30% by weight of the total weight. Even if the same erythritol is used, when its average particle size is about 30 to about 35 µm, the disintegrating property may sometimes become poor when the proportion of the disintegrant in the coating on a granule and in the inside of the granule exceeds 20% by weight of the total weight. When an excipient is mannitol and its average particle size is about 50 µm, the disintegrating property may sometimes become poor when the proportion of the disintegrant in the coating on a granule and in the inside of the granule exceeds 30% by weight of the total weight.

A more preferable value taking into account the texture depends on the type of an excipient contained in the inside of the granule when an excipient described below is used together. When erythritol is used as an excipient, it is particularly preferably present at 4 to 8% by weight in the inside of the granule relative to a whole tablet, and at 4 to 8% by weight in the coating relative to a whole tablet. When mannitol is used as an excipient, however, the preferred range of the content of the disintegrant is the same as described above, even taking into account the texture.

The typical average particle size of the disintegrant used in the present invention is about 10 to about 100 µm. In general, larger particles are advantageous in terms of disintegrating property and permeation speed. On the other hand, smaller particles with a larger number of binding sites are advantageous in terms of compression moldability. A smaller particle size is also preferable in terms of texture.

Preferably, the granule of the present invention contains voids in the inside thereof, as far as they do not damage practical hardness. Retention of such voids in the inside of the granule improves compression moldability and/or rapid disintegrating property.

In order to retain such voids in a granule, a tablet may be produced, for example, by preparing a granule containing a disintegrant swollen with water and/or ethanol and then coating the granule with the disintegrant, followed by drying and compression molding. When a binder is not added, the structure of a granule before compression molding may be destroyed and thus a desired function of a tablet may be lost, if a drying method with a large load such as fluidized bed drying is adopted. In this case, ventilation drying with a small load is preferably adopted.

Examples of pharmaceutically acceptable additives used in the tablet of the present invention can include excipients, lubricants, pH adjusters, taste-masking agents, sweeteners, acidifiers, refrigerants, foaming agents, preservatives, fluidizers, antioxidants, colorants, stabilizers, surfactants, buffering agents, flavors, binders and drug solubilizers. A person skilled in the art may immediately list specific examples of these additives.

These additives can be appropriately formulated in the inside of a granule, in the outside of a granule coated with a disintegrant, in the coating of a disintegrant and in all these, as far as they do not damage the advantages of the present invention. It is preferable, however, not to contain a binder in order not to deteriorate good feeling in the oral cavity and to improve the disintegrating property.

Any excipient used for pharmaceutical preparations can be used without limitation, but examples of excipients used in the tablet of the present invention can include sugars such as erythritol, mannitol, xylitol, sorbitol, lactitol, paratinit, paratinose, maltitol, maltose, trehalose, lactose, sucrose, glucose, olygosaccharides, fructose and maltose and the like. One or two or more kinds of these excipients can be used. Particularly, it is preferable to use one or more selected from erythritol and mannitol.

The excipient used in the present invention is contained in the inside of a granule constituting a tablet and/or in a coating of a disintegrant and/or in the outside of a granule coated with a disintegrant. Although addition of an excipient is required to secure compression moldability depending on the type of a drug, whether or not addition of such an excipient is required can be easily determined by ordinary preliminary examination by a person skilled in the art.

A preferable range of an excipient particle size may be easily found through examination of condition, as required, by a person skilled in the art. The typical particle size of a disintegrant is about 20 to about 40 μm. In general, a smaller particle size is advantageous in terms of disintegrating property and texture, but a particle size of an excipient hardly affects compression moldability.

Any lubricant used for pharmaceutical preparation can be used without limitation. Examples of the lubricant used in the tablet of the present invention can include light anhydrous silicic acid, magnesium stearate, stearic acid, calcium stearate, aluminum stearate, aluminum monostearate, sucrose fatty acid esters, polyethylene glycol, sodium stearyl fumarate, stearyl alcohol, talc, titanium oxide, hydrous silicon dioxide, magnesium silicate, synthetic aluminum silicate, calcium hydrogen phosphate, hardened castor oil, hardened rapeseed oil, Carnauba Wax, bees wax, microcrystalline wax and sodium lauryl sulfate. One or two or more kinds of these lubricants can be used. Among these, it is preferable to use one or more selected from light anhydrous silicic acid and magnesium stearate. Particularly, a combination of silicic anhydride contained in the inside of a granule and magnesium stearate contained in the outside of the granule is preferable.

The shape of the table of the present invention is not particularly limited, as far as it can be produced without difficulty using an ordinary manufacturing apparatus or a manufacturing apparatus with some modifications. A disc shape that is a general concept for tablets can be mentioned as a typical example. The whole size is not particularly limited. For example, the shorter diameter (diameter for a disc tablet) is appropriately in the range of 6 to 20 mm, preferably 8 to 12 mm. The thickness is neither particularly limited, but appropriately 1 to 10 mm, preferably 2 to 8 mm.

The tablet of the present invention can be produced without difficulty using an ordinary manufacturing apparatus or a manufacturing apparatus with some modifications. For example, the tablet is manufactured by coating a granule containing a disintegrant and by necessity one or more kinds of pharmaceutically acceptable additives with a disintegrant, and by compression molding the granule thus coated together with one or more kinds of pharmaceutically acceptable additives.

In order to incorporate one or more kinds of pharmaceutically acceptable additives in the inside of a granule, the granule may be prepared after mixing a disintegrant before preparation of a granule with required additive(s). In order to incorporate one or more kinds of pharmaceutically acceptable additives in the outside of a granule coated with a disintegrant, the granule coated with a disintegrant may be subjected to compression molding after mixing with required additives to form a tablet.

The present invention is also a granule used for molding such an intraorally rapidly disintegrating tablet, in which the granule contains a disintegrant in the inside thereof and may contain a drug in the inside thereof and is coated with a disintegrant. The granule may contain one or more kinds of pharmaceutically acceptable additives in the inside thereof. Specific examples and preferable examples of these additives can be as exemplified above, and erythritol and mannitol are particularly preferable.

Further, the granule preferably contains voids in the inside thereof and preferably contains no binder.

Crospovidone is preferable as a disintegrant contained in the inside of a granule and in a coating.

EXAMPLES

The present invention will be illustrated referring to Examples, but the present invention is not limited by these Examples.

[Evaluation Methods]

The following evaluation methods were employed in Examples and Comparative Examples below.

a) "Hardness" was measured using a tablet hardness tester TH-203MP of Toyama Sangyo Co., Ltd.

b) "Friability" was measured using a friability tester of Kayagaki Irika Kogyo. Specifically, 55 tablets were charged into the tester and rotated 100 times. The friability was expressed in % according to (Initial weight−Weight after test)/Initial weight.

c) "Sensory evaluation" was conducted by measuring the time required to disintegrate a tablet in the oral cavity without chewing. For the placebo preparations in Examples/Comparative Examples, a mean from N=6 from one adult male was used. For three active preparations in Examples, a mean from N=3 from 3 adult males was used.

d) "Disintegration test of the Japanese Pharmacopoeia" was conducted in accordance with the "Disintegration test method of the Japanese Pharmacopoeia." MiliQ water was used as a test liquid.

e) "Penetration time" was measured as the time required for water to penetrate into a whole tablet after 1 mL of MiliQ water colored with Blue No. 1 was dropped onto a petri dish and a tablet was placed on it.

Example 1

D-mannitol, 264.4 g (Towa Chemical Industry Co., Ltd., Trade Name: Mannit P (average particle size: about 50 μm), the same in the following examples), 14.2 g of light anhydrous silicic acid (Freund Corporation) and 20.3 g of crospovidone (ISP, Trade Name; Polyplasdone XL-10 (average particle size according to the manufacturer's information: 30 μm), the same in the following examples, unless otherwise stated) were fed into a fluidized bed granulation dryer (Powrex Corp., LAB-1). Purified water containing 11.0 g of swollen crospovidone was sprayed to the mixture to obtain granules. The granules were charged with 48.8 g of crospovidone and powder-coated with purified water containing 1.2 g of swollen crospovidone. To 177.0 g of the granules coated with the disintegrant thus obtained, 20.0 g of Febuxostat (Teijin Pharma Limited) and 3.0 g of calcium stearate (NOF CORPORATION) were added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

Example 2

D-mannitol, 264.4 g (Towa Chemical Industry Co., Ltd.), 14.2 g of light anhydrous silicic acid (Freund Corporation) and 20.3 g of crospovidone (ISP) were fed into a fluidized bed granulation dryer (Powrex Corp., LAB-1). Purified water containing 11.0 g of swollen crospovidone was sprayed to the mixture to obtain granules. The granules were charged with 48.8 g of crospovidone and powder-coated with purified water containing 1.2 g of swollen crospovidone. To 177.0 g of the granules coated with the disintegrant thus obtained, 20.0 g of ascorbic acid (Takeda Pharmaceutical Company Limited) and 3.0 g of calcium stearate (NOF CORPORATION) were added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

Reference Example 1

D-mannitol, 264.4 g (Towa Chemical Industry Co., Ltd.), 14.2 g of light anhydrous silicic acid (Freund Corporation) and 20.3 g of crospovidone (ISP) were fed into a fluidized bed granulation dryer (Powrex Corp., LAB-1). Purified water containing 11.0 g of swollen crospovidone was sprayed to the mixture to obtain granules. The granules were charged with 48.8 g of crospovidone and powder-coated with purified water containing 1.2 g of swollen crospovidone. To 177.0 g of the granules coated with the disintegrant thus obtained, 20.0 g of ambroxol hydrochloride (Nippon Bulk Yakuhin Co., Ltd.) and 3.0 g of calcium stearate (NOF CORPORATION) were added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

The results of evaluation of the tablets of Examples 1 to 2 and Reference Example 3 are shown in Table 1.

The results show that the tablets of the present invention satisfy all the evaluation items for hardness, compression moldability (friability) and disintegrating property. In addition, it has been shown that all these effects can be achieved regardless of the type of drug.

Example 3

Erythritol, 296.0 g (NIKKEN Fine Chemicals Co., Ltd, Grade 100M (average particle size: about 15 μm), the same in Comparative Examples 1 and 2 below), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 21.9 g of crospovidone and powder-coated with purified water containing 1.1 g of swollen crospovidone. The granules coated with the disintegrant were subjected to ventilation drying in a dryer. To 197.1 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf.

Comparative Example 1

Erythritol, 325.2 g (NIKKEN Fine Chemicals Co., Ltd) and 12.8 g of light anhydrous silicic acid (Freund Corporation) were fed into a fluidized bed granulation dryer (Powrex Corp., LAB-1). Purified water was sprayed to the mixture to obtain granules. The granules were charged with 22.0 g of crospovidone and powder-coated with purified water. The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf. This Comparative Example was conducted to confirm the effect of presence of the disintegrant in the inside of the a granule on moldability and rapid disintegrating property, and a tablet containing no disintegrant in a granule was thus produced.

TABLE 1

| | Tableting pressure (KN) | Weight (mg) | Hardness (kgf) | Friability (%) | Sensory evaluation | Disintegration time (sec) | | Texture |
| | | | | | | JP Disintegration test | Penetration time | |
| --- | --- | --- | --- | --- | --- | --- | --- | --- |
| Example 1 Febuxostat | 9.3 | 120.3 | 5.4 | 0.3 | 14.3 | 18.3 | 18.7 | Good |
| Example 2 Ascorbic acid | 11.5 | 119.7 | 5.3 | 0.2 | 11.7 | 17.3 | 6.7 | Good |
| Reference Example 1 Ambroxol hydrochloride | 11.0 | 119.5 | 5.7 | 0.2 | 8.6 | 15.3 | 5.5 | Good |

Comparative Example 2

Erythritol, 310.8 g (NIKKEN Fine Chemicals Co., Ltd), 12.8 g of light anhydrous silicic acid (Freund Corporation) and 14.6 g of hydroxypropyl cellulose (Nippon Soda Co., Ltd., HPC-L) were fed into a fluidized bed granulation dryer (Powrex Corp., LAB-1). Purified water was sprayed to the mixture to obtain granules. The granules were charged with 21.9 g of crospovidone and powder-coated with purified water. The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf. This Comparative Example was conducted by further adding a binder, since the granules could not be molded due to insufficient granule binding powder, and as a result rapid disintegrating property could not be verified in Comparative Example 1. The results of evaluation of the tablets of Example 3, Comparative Example 1 and Comparative Example 2 are shown in Table 2.

However, the mechanism by which compression moldability is improved by the presence of a disintegrant both in the inside of a granule and in a coating has not been elucidated.

Example 4

D-mannitol, 318.0 g (Towa Chemical Industry Co., Ltd.), 12.8 g of light anhydrous silicic acid (Freund Corporation) and 9.2 g of crospovidone (ISP) were fed into a fluidized bed granulation dryer (Powrex Corp., LAB-1). Purified water containing 5.0 g of swollen crospovidone was sprayed to the mixture to obtain granules. The granules were charged with 14.6 g of crospovidone and powder-coated with purified water containing 0.6 g of swollen crospovidone. The granules coated with the disintegrant were subjected to ventilation drying in a dryer. To 197.0 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

TABLE 2

| | Disintegrant (%) | | | | | | | | Disintegration time (sec) | | |
|---|---|---|---|---|---|---|---|---|---|---|---|
| | Coating | Inside of granule | Addition during mixing | Binder (%) | Method of drying | Tableting pressure (KN) | Weight (mg) | Hardness (kgf) | Friability (%) | Sensory evaluation | Penetration speed | Texture |
| Example 3 | 6 | 8 | 0 | 0 | Ventilation drying | 7.2 | 199.6 | 3.1 | 0.5 | 6.6 | 8.2 | Good |
| Comparative Example 1 No disintegrant inside of granule | 6 | 0 | 0 | 0 | Ventilation drying | 14.0 | 201.4 | 0.6 | Immeasurable | 14.9 | 11.5 | Good |
| Comparative Example 2 No disintegrant inside of granule With binder | 6 | 0 | 0 | 4 | Ventilation drying | 9.5 | 201.7 | 3.3 | 0.9 | 12.6 | 16.7 | Good |

According to the results, the tablet of Comparative Example 1 had the hardness of only up to 0.6 kgf even when the tableting pressure about 2 times that for the tablets of Example 3 was applied and was so friable that friability could not measured with the friability tester. The tablets of Comparative Example 1 are thus inappropriate for practical use. This result shows that the presence of a disintegrant in the inside of a granule is essential for moldability of the tablets of Example 3.

In Comparative Example 2, the tablets were formed with the binder added to the formulation of Comparative Example 1. The tablet of Comparative Example 2, although containing the binder, was more friable than that of Example 3, still had insufficient compression moldability, and had a disintegration time about 2 times that in Example 3. The result shows that the presence of a disintegrant in the inside of a granule improves the disintegrating property and compression moldability.

Example 5

D-mannitol, 303.4 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 14.6 g of crospovidone and powder-coated with purified water containing 1.1 g of swollen crospovidone. The granules coated with the disintegrant were subjected to ventilation drying in a dryer. To 197.0 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

Example 6

D-mannitol, 296.1 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 21.9 g of crospovidone and powder-coated with purified water containing 1.1 g of swollen crospovidone. The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Example 7

D-mannitol, 288.8 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 29.2 g of crospovidone and powder-coated with purified water containing 1.1 g of swollen crospovidone. The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Example 8

D-mannitol, 281.5 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 36.5 g of crospovidone and powder-coated with purified water containing 1.1 g of swollen crospovidone. The granules coated with the disintegrant were subjected to ventilation drying in a dryer. To 197.3 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Example 9

D-mannitol, 237.5 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 80.4 g of crospovidone and powder-coated with purified water containing 1.1 g of swollen crospovidone. The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Example 10

D-mannitol, 318.0 g (Towa Chemical Industry Co., Ltd.), 12.8 g of light anhydrous silicic acid (Freund Corporation) and 9.1 g of crospovidone (ISP) were fed into a fluidized bed granulation dryer (Powrex Corp., LAB-1). Purified water containing 5.0 g of swollen crospovidone was sprayed to the mixture to obtain granules. The granules were charged with 14.6 g of crospovidone and powder-coated with purified water containing 0.6 g of swollen crospovidone. The granules coated with the disintegrant were dried in a fluidized bed granulation dryer. To 196.9 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Comparative Example 3

D-mannitol, 318.0 g (Towa Chemical Industry Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 11.0 g of swollen crospovidone was sprayed to the mixture to obtain granules. The granules were subjected to ventilation drying in a dryer. To 196.8 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a $\phi$8 mm flat punch with a cleavage line and a round edge to obtain hardness of about 5 kgf.

Comparative Example 4

D-mannitol, 318.0 g (Towa Chemical Industry Co., Ltd.) and 12.8 g of light anhydrous silicic acid (Freund Corporation) were fed into a fluidized bed granulation dryer (Powrex Corp., LAB-1). Purified water was sprayed to the mixture to obtain granules. The granules were charged with 29.3 g of crospovidone and powder-coated with purified water. The granules coated with the disintegrant were subjected to ventilation drying in a dryer. To 197.0 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

Comparative Example 5

D-mannitol, 331.3 g (Towa Chemical Industry Co., Ltd.), 13.2 g of light anhydrous silicic acid (Freund Corporation) and 9.5 g of crospovidone (ISP) were fed into a fluidized bed granulation dryer (Powrex Corp., LAB-1). Purified water containing 5.7 g of swollen crospovidone was sprayed to the mixture to obtain granules. The granules were subjected to ventilation drying in a dryer. To 189.0 g of the granules thus obtained, 8.0 g of crospovidone (ISP) was added followed by primary mixing. Then, 3.0 g of calcium stearate (NOF CORPORATION) was added followed by secondary mixing. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf.

The results of evaluation of the tablets of Examples 4 to 10 and Comparative Examples 3 to 5 are shown in Table 3.

In Examples 4 to 9, mannitol was used as an excipient in the inside of the granule and the proportions of the disintegrant (% by weight) in the inside of the granule and in the coating were varied. All these tablets were shown to satisfy all the evaluation items for hardness, compression moldability (friability) and disintegrating property. The results show that the evaluation items are satisfied when the proportions of a disintegrant both in the inside of a granule and in the coating may be at least 4 to 20% by weight, and that texture and disintegrating property are slightly reduced when the content of the disintegrant in the coating is more than 20% by weight (Example 9).

Further, when fluidized bed drying was used as a drying method instead of ventilation drying, the advantage of the present invention was also achieved, but a slightly higher tableting pressure was required (Example 10). Accordingly, ventilation drying has been shown to be more desirable than the fluidized bed drying. The reason for this is considered to be the following: Fluidized bed drying causes some changes in the granule structure and one of the changes is a reduction in the number and size of voids in a granule as compared to the case of ventilation drying, leading to deterioration in compression moldability.

The tablet of Comparative Example 3 was not coated by a disintegrant. The tablet was inferior to the tablet of the present invention in disintegrating property and compression moldability, and the tableting pressure exceeded the practical limit.

TABLE 3

| | Disintegrant (%) | | | | | | | | Disintegration time (sec) | | |
|---|---|---|---|---|---|---|---|---|---|---|---|
| | Coating | Inside of granule | Addition during mixing | Method of drying | Tableting pressure (KN) | Weight (mg) | Hardness (kgf) | Friability (%) | Sensory evaluation | Penetration speed | Texture |
| Example 4 | 4 | 4 | 0 | Ventilation drying | 12.1 | 119.7 | 5.5 | 0.3 | 6.1 | 5.7 | Good |
| Example 5 | 4 | 8 | 0 | Ventilation drying | 12.2 | 120.1 | 5.7 | 0.2 | 5.7 | 4.5 | Good |
| Example 6 | 6 | 8 | 0 | Ventilation drying | 11.1 | 120.8 | 5.3 | 0.3 | 5.7 | 5.4 | Good |
| Example 7 | 8 | 8 | 0 | Ventilation drying | 11.5 | 121.1 | 5.3 | 0.2 | 6.2 | 5.8 | Good |
| Example 8 | 10 | 8 | 0 | Ventilation drying | 10.3 | 120.7 | 5.2 | 0.2 | 6.3 | 5.1 | Good |
| Example 9 | 22 | 8 | 0 | Ventilation drying | 8.5 | 120.8 | 4.9 | 0.1 | 8.7 | 7.7 | Good Slightly more coarse than Examples 4 to 8 The tablet had a hard core and was more difficult to dissolve than those in Examples 4 to 8 |
| Example 10 | 4 | 4 | 0 | Drying in fluidized bed | 14.5 | 120.2 | 5.7 | 0.2 | 6.9 | 5.8 | |
| Comparative Example 3 | 0 | 8 | 0 | Ventilation drying | 19.0 | 120.5 | 5.4 | 0.4 | 10.4 | 9.6 | Good The tablet had a hard core and was more difficult to dissolve than those in Examples 4 to 8 |
| Comparative Example 4 | 8 | 0 | 0 | Ventilation drying | 16.1 | 120.0 | 5.6 | 0.3 | 12.3 | 11.9 | Good The tablet had a hard core and was more difficult to dissolve than those in Examples 4 to 8 |
| Comparative Example 5 | 0 | 4 | 4 | Ventilation drying | 17.5 | 120.3 | 5.5 | 0.3 | 8.6 | 7.7 | Good |

The tablet of Comparative Example 4 contained no disintegrant in the inside of the granule. The tablet was also much inferior to the tablet of the present invention in disintegrating property and compression moldability, and the tableting pressure exceeded the practical limit.

The tablet of Comparative Example 5 contained a disintegrant in the inside of the granule and also in the outside of the granule, but was not coated with the disintegrant. The tablet required higher tableting pressure than the tablet of the present invention and was inferior in compression moldability. It has been confirmed that it is not sufficient that a disintegrant is merely contained in the outside of a granule in addition to in the inside of a granule and that coating with a disintegrant is also required.

Accordingly, it is shown that the presence of a disintegrant in the inside of a granule and in a coating on the granule is required for good compression moldability, disintegrating property and sufficient hardness. Even when the tablets had the same total content of the disintegrant (Example 4 in Table 3 and Comparative Examples 3 to 5), only the tablet of the present invention (Example 4 in Table 3) had good compression moldability, disintegrating property and sufficient hardness. These results indicate that the present invention has such an advantage that required properties for a rapidly disintegrating tablet can be achieved with a smaller amount of a disintegrant.

Example 11

Erythritol, 318.0 g (NIKKEN Fine Chemicals Co., Ltd, Grade 50M (average particle size: about 35 μm), the same in Examples 12 to 15 below), 12.7 g of light anhydrous silicic acid (Freund Corporation) and 9.1 g of crospovidone (ISP) were fed into a fluidized bed granulation dryer (Powrex Corp., LAB-1). Purified water containing 5.0 g of swollen crospovidone was sprayed to the mixture to obtain granules. The granules were charged with 14.6 g of crospovidone and powder-coated with purified water containing 0.6 g of swollen crospovidone. The granules coated with the disintegrant were subjected to ventilation drying in a dryer. To 196.9 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf. Evaluation was performed after the tablet was stored in a tightly-sealed container at room temperature for 3 days to stabilize hardness and friability.

Example 12

Erythritol, 303.4 g (NIKKEN Fine Chemicals Co., Ltd.), 12.9 g of light anhydrous silicic acid (Freund Corporation) and 13.7 g of crospovidone (ISP) were fed into a fluidized bed granulation dryer (Powrex Corp., LAB-1). Purified water containing 7.4 g of swollen crospovidone was sprayed to the mixture to obtain granules. The granules were charged with 21.9 g of crospovidone and powder-coated with purified water containing 0.8 g of swollen crospovidone. The granules coated with the disintegrant were subjected to ventilation drying in a dryer. To 197.2 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf. Evaluation was performed after the tablet was stored in a tightly-sealed container at room temperature for 3 days to stabilize hardness and friability.

Example 13

Erythritol, 288.7 g (NIKKEN Fine Chemicals Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 29.1 g of crospovidone and powder-coated with purified water containing 1.1 g of swollen crospovidone. The granules coated with the disintegrant were subjected to ventilation drying in a dryer. To 197.1 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf. Evaluation was performed after the tablet was stored in a tightly-sealed container at room temperature for 3 days to stabilize hardness and friability.

Example 14

Erythritol, 274.1 g (NIKKEN Fine Chemicals Co., Ltd.), 12.8 g of light anhydrous silicic acid (Freund Corporation) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 43.8 g of crospovidone and powder-coated with purified water containing 1.1 g of swollen crospovidone. The granules coated with the disintegrant were subjected to ventilation drying in a dryer. To 197.1 g of the granules coated with the disintegrant thus obtained, 2.9 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf. Evaluation was performed after the tablet was stored in a tightly-sealed container at room temperature for 3 days to stabilize hardness and friability.

Example 15

Erythritol, 237.5 g (NIKKEN Fine Chemicals Co., Ltd.), 12.8 g of light anhydrous silicic acid (Freund Corporation) and 69.6 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 29.3 g of crospovidone and powder-coated with purified water containing 1.1 g of swollen crospovidone. The granules coated with the disintegrant were subjected to ventilation drying in a dryer. To 197.2 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 120 mg and tableting was conducted using a φ8 mm flat punch with a cleavage line and a round edge to obtain hardness of about 5 kgf. Evaluation was performed after the tablet was stored in a tightly-sealed container at room temperature for 3 days to stabilize hardness and friability.

The results of evaluation of the tablets of Examples 11 to 15 are shown in Table 4.

(XL-10) was sprayed to the mixture to obtain granules. The granules were charged with 43.9 g of crospovidone (XL-10) and powder-coated with purified water containing 1.1 g of swollen crospovidone (XL-10). The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf.

TABLE 4

| | Disintegrant (%) | | | | | | | Disintegration time (sec) | | |
| --- | --- | --- | --- | --- | --- | --- | --- | --- | --- | --- |
| | Coating | Inside of granule | Addition during mixing | Method of drying | Tableting pressure (KN) | Weight (mg) | Hardness (kgf) | Friability (%) | Sensory evaluation | Penetration speed | Texture |
| Example 11 | 4 | 4 | 0 | Ventilation drying | 8.1 | 120.7 | 3.1 (during manufacturing 2.3) | Immeasurable | 8.2 | 5.5 | Good |
| Example 12 | 6 | 6 | 0 | Ventilation drying | 10.5 | 121.2 | 4.8 (during manufacturing 3.4) | 0.4 | 14.6 | 7.9 | Good |
| Example 13 | 8 | 8 | 0 | Ventilation drying | 8.7 | 119.5 | 4.7 (during manufacturing 3.5) | 0.4 | 22.7 | 10.1 | Good The tablet had a hard core and was difficult to dissolve |
| Example 14 | 8 | 12 | 0 | Ventilation drying | 8.1 | 120.0 | 4.4 (during manufacturing 3.5) | 0.3 | 29.2 | 13.1 | Good The tablet had a hard core and was difficult to dissolve |

In Examples 11 to 15, erythritol was used as an excipient in the inside the granule, and the proportions of the disintegrant (% by weight) in the inside of the granule and in the coating were varied. The hardness, compression moldability (friability) and disintegrating property of all these tablets were within the allowable range. As compared with the results in Table 3, however, the ranges tend to be narrower than those obtained with mannitol. In other words, when erythritol is used, the evaluation items are satisfied if the proportion of a disintegrant both in the inside of a granule and in a coating may be at least 4 to 8% by weight. However, when the content of the disintegrant in the inside of a granule is 8% by weight or more, texture and disintegrating property are slightly deteriorated (Example 13-14), and when the content exceeds 20% by weight, particularly disintegrating property is reduced (Example 15).

For all the tablets, the hardness increased 3 days after manufacturing. It has been shown that hardness is increased by some mechanism over time after manufacturing at least in the case of using erythritol.

Example 16

Ascorbic acid, 36.6 g (Takeda Pharmaceutical Company Limited, 80 mesh), 201.0 g of D-mannitol (Towa Chemical Industry Co., Ltd., Mannit P), 12.8 g of light anhydrous silicic acid (Freund Corporation, Adsolider 101) and 54.8 g of crospovidone (ISP, Polyplasdon XL-10) were fed into a fluidized bed granulation dryer (Powrex Corp., LAB-1). Purified water containing 9.9 g of swollen crospovidone Example 17

Ascorbic acid, 36.5 g (Takeda Pharmaceutical Company Limited, 80 mesh), 201.0 g of D-mannitol (Towa Chemical Industry Co., Ltd., Mannit P), 12.8 g of light anhydrous silicic acid (Freund Corporation, Adsolider 101) and 54.8 g of crospovidone (ISP, Polyplasdon INF-10 (average particle size according to the manufacturer's information: 11 μm)) were fed into a fluidized bed granulation dryer (Powrex Corp., LAB-1). Purified water containing 9.9 g of swollen crospovidone (INF-10) was sprayed to the mixture to obtain granules. The granules were charged with 43.9 g of crospovidone (INF-10) and powder-coated with purified water containing 1.1 g of swollen crospovidone (INF-10). The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf.

Example 18

Ascorbic acid, 36.6 g (Takeda Pharmaceutical Company Limited, 80 mesh), 201.0 g of D-mannitol (Towa Chemical Industry Co., Ltd., Mannit P), 12.8 g of light anhydrous silicic acid (Freund Corporation, Adsolider 101) and 54.8 g of crospovidone (ISP, Polyplasdon INF-10) were fed into a fluidized bed granulation dryer (Powrex Corp., LAB-1). Purified water containing 9.9 g of swollen crospovidone (INF-10) was sprayed to the mixture to obtain granules. The granules were charged with 43.9 g of crospovidone (XL-10) and powder-coated with purified water containing 1.1 g of swollen crospovidone (INF-10). The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf.

Example 19

Ascorbic acid, 36.5 g (Takeda Pharmaceutical Company Limited, 80 mesh), 201.1 g of D-mannitol (Towa Chemical Industry Co., Ltd., Mannit P), 12.8 g of light anhydrous silicic acid (Freund Corporation, Adsolider 101) and 54.8 g of crospovidone (ISP, Polyplasdon INF-10) were fed into a fluidized bed granulation dryer (Powrex Corp., LAB-1). Purified water containing 9.9 g of swollen crospovidone (INF-10) was sprayed to the mixture to obtain granules. The granules were charged with 43.9 g of crospovidone (XL, average particle size according to the manufacturer's information: 100 μm) and powder-coated with purified water containing 1.1 g of swollen crospovidone (INF-10). The granules coated with the disintegrant were subjected to ventilation drying in a dryer. To 197.0 g of the granules coated with the disintegrant thus obtained, 3.0 g of calcium stearate (NOF CORPORATION) was added and mixed. The mixture was then subjected to compression molding with a rotary tableting machine (HATA IRON WORKS CO., LTD., HT-AP6SS-U). The molding conditions were as follows: tablet weight was 200 mg and tableting was conducted using a φ10 mm flat punch with a cleavage line and a round edge to obtain hardness of about 3 kgf.

The results of evaluation of the tablets of Examples 16 to 19 are shown in Table 5. The numbers in the parentheses in the item of disintegrant (%) in Table 5 are average particle sizes according to information supplied by the manufacturer.

In Examples 16 to 19, the proportions (% by weight) of the disintegrant in the inside of the granule and in the coating were kept constant and the average particle size of the disintegrant used was varied. When the disintegrant with an average particle size of 11 μm was used both in the inside of the granule and in the coating (Example 17), the disintegration time and the permeation time were slightly delayed as compared with those obtained with the disintegrant with an average particle size of 31 μm (Example 16). When the average particle size was 11 μm in the inside of the granule and 31 μm in the coating (Example 18), all the moldability, disintegration time, and permeation time were superior to those obtained with the disintegrant with an average particle size of 11 μm both in the inside of the granule and in the coating (Example 17). It has been shown that when the average particle size was 11 μm in the inside of the granule and 100 μm in the coating (Example 19), both the disintegration time and permeation time were shorter than those of the tablet coated with the granule with an average particle size of 31 μm (Example 18). The above results show the followings: in terms of disintegrating property and permeation time, it is advantageous to use a disintegrant with a larger particle size, while in terms of moldability, it is advantageous to use a disintegrant with a smaller particle size. However, excessive fine particles of crospovidone on the surface of a granule cause sticking (gloss loss of a pestle).

[Example 20] Granule Surface Analysis with x-Ray Photoelectron Spectrometer (XPS, ESCA)

The amount of nitrogen on the surface of a granule prepared and that of a granule coated with a disintegrant was measured with an ESCA to confirm that coating with crospovidone was provided by the disintegrant coating operation described above. This measurement was conducted at Nitto Analytical Techno Center by commission.

ESCA is one of the representative surface analysis apparatuses and used for analysis of elements and the state of chemical bond in the region at the depth of several nm from a solid surface. When soft X-ray at a specific energy is irradiated onto the surface of a solid sample under high vacuum, photoelectrons are emitted from the sample by the photoelectron effect. The photoelectrons are introduced to an analyzer, where the photoelectrons are separated according to the kinetic energy of electrons and detected as spectra. Only photoelectrons in the region at the depth of several nm

TABLE 5

| | Disintegrant (%) | | | | | | | | Disintegration time (sec) | | |
|---|---|---|---|---|---|---|---|---|---|---|---|
| | Coating | Inside of granule | Addition during mixing | Method of drying | Tableting pressure (KN) | Weight (mg) | Hardness (kgf) | Friability (%) | Sensory evaluation | Penetration speed | Texture |
| Example 16 | 12 (31 μm) | 18 (31 μm) | 0 | Ventilation drying | 8.0 Occurrence of sticking (chipping of a tablet) | 199.4 | 3.3 | 0.3 | 7.9 | 7.1 | Good |
| Example 17 | 12 (11 μm) | 18 (11 μm) | 0 | Ventilation drying | 6.6 Occurrence of sticking (gloss loss of a pestle) | 198.9 | 3.0 | 0.2 | 10.6 | 10.2 | Good |
| Example 18 | 12 (31 μm) | 18 (11 μm) | 0 | Ventilation drying | 7.8 | 201.0 | 2.8 | 0.2 | 9.1 | 7.4 | Good |
| Example 19 | 12 (100 μm) | 18 (11 μm) | 0 | Ventilation drying | 7.2 Occurrence of sticking (chipping of a tablet) | 198.9 | 3.0 | 0.2 | 8.4 | 6.7 | Good | escaping from the sample surface without inelastic scattering are detected as a peak and used for analysis. A binding energy is obtained as a difference calculated by subtracting the kinetic energy of photoelectrons from the energy of irradiated soft X-ray. Since a core electron of various atoms has an intrinsic binding energy, the kinds of elements can be determined from the binding energies of electrons detected and the proportion of elements from signal strengths. In this case, measurement was conducted on a nitrogen atom etc. specific to crospovidone.

Preparation of Sample 1:

D-mannitol, 274.1 g (Towa Chemical Industry Co., Ltd.), 12.8 g of light anhydrous silicic acid (Freund Industrial Co., Ltd.) and 18.3 g of crospovidone (ISP) were fed into a fluidized bed granulation dryer (Powrex Corp., LAB-1). Purified water containing 9.9 g of swollen crospovidone was sprayed to the mixture to obtain granules. The granules were charged with 43.8 g of crospovidone and powder-coated with purified water containing 1.1 g of swollen crospovidone. The granules coated with the disintegrant were subjected to ventilation drying in a dryer.

Preparation of Sample 2:

D-mannitol, 274.1 g (Towa Chemical Industry Co., Ltd.), 12.8 g of light anhydrous silicic acid (Freund Corporation) and 73.1 g of crospovidone (ISP) were fed into a fluidized bed granulation dryer (Powrex Corp., LAB-1). Purified water was sprayed to the mixture to obtain granules. The granules were dried in the fluidized bed granulation dryer.

Sample 2 is at a stage of prepared granule and Sample 1 is a granule coated with crospovidone. Measurement was conducted on arbitrary 5 samples each, and "n" is a sample number. The measurement conditions were as follows:
ESCA; Quantum 2000 (ULVAC-PHI Inc.)
X-ray Setting; point analysis at 100 μm φ[25 W (15 kV)]
X-ray source; monochromated $AlK_\alpha$
Photoelectron ejection angle; 45°
Neutralization condition; Combined use of neutralization gun and ion gun (neutralization mode)
The measurement results are shown in Table 6.

TABLE 6

| Analytical sample | C | N | O | Si |
|---|---|---|---|---|
| Sample 1 n1 | 31.7 | 0.7 | 55.0 | 12.6 |
| Sample 1 n2 | 39.4 | 2.9 | 46.6 | 11.1 |
| Sample 1 n3 | 33.5 | 0.7 | 54.1 | 11.7 |
| Sample 1 n4 | 37.1 | 2.3 | 49.1 | 11.5 |
| Sample 1 n5 | 40.4 | 2.7 | 46.7 | 10.2 |
| Sample 2 n1 | 35.0 | 0.4 | 54.2 | 10.4 |
| Sample 2 n2 | 48.9 | — | 49.8 | 1.3 |
| Sample 2 n3 | 51.4 | — | 48.6 | — |
| Sample 2 n4 | 46.8 | — | 49.9 | 3.3 |
| Sample 2 n5 | 42.7 | 0.3 | 51.3 | 5.7 |

"—" is the assay limit or lower (N, Si < 0.2%).

According to the results, four elements, C, N, O and Si, were detected in both Samples 1 and 2. The detection of N and Si indicates the presence of crospovidone and a silicic acid component, respectively. The element ratio of nitrogen in Sample 2 was less than 0.5% for all samples, while the element ratio of nitrogen in Sample 1 ranged from 0.7% to 2.9%. Accordingly, the amount of nitrogen on the surface was larger in Sample 1, confirming that the surface was actually coated with crospovidone by the crospovidone coating operation.

[Example 21] Surface Analysis with Time-of-Flight Secondary Ion Mass Spectrometer (TOF-SIMS)

The investigation similar to that in Example 20 was conducted with a time-of-flight secondary ion mass spectrometer (TOF-SIMS). In other words, it was confirmed that coating with crospovidone was provided by the disintegrant coating operation described above. This measurement was conducted at Nitto Analytical Techno Center by commission.

TOF-SIMS is an apparatus to determine what kinds of components (atoms, molecules) are present on the outermost surface of a solid sample. It can detect extremely minor components present in the order of ppm and can be applicable to organics and inorganics. When a high speed ion beam (primary ion) is sputtered onto the surface of a solid sample in high vacuum, components on the surface are ejected by the sputtering phenomenon. Positively or negatively charged ions (secondary ions) generated upon sputtering are allowed to fly in one direction by the electric field and detected at a certain distance away. Secondary ions having various masses are produced depending on the composition of the surface of a sample upon sputtering. Lighter ions fly faster and heavier ions fly slower. When the time of flight from production to detection of secondary ions is measured, the mass of the secondary ions can be calculated. In TOF-SIMS, the amount of primary ions irradiated is remarkably small. Organic compounds are therefore ionized while maintaining their chemical structures and the structures of organic compounds can be elucidated from their mass spectra. Since only secondary ions produced on the outermost surface of a solid sample can be emitted into a vacuum, the information concerning the outermost surface (a depth of about several Angstroms) can be obtained. In addition, scanning of a primary ion beam allows measurement of an ion image (mapping) of the surface of the sample.

Samples 1 and 2 were retained on an adhesive tape, fixed on a holder for TOF-SIMS measurement and measured. The measurement conditions were as follows:
TOF-SIMS; TRIFT2 (ULVAC-PHI Inc.)
Primary ion; $^{69}Ga^+$ (accelerating voltage 15 kV)

As a result, the positive and negative secondary ion mass spectra and positive and negative ion images of the surface of Samples 1 and 2 were obtained. Crospovidone, silicic acid component and mannitol were detected from all the samples. Ions characteristic for crospovidone are $C_6H_{10}NO^+$, $CN^-$, $CNO^-$, etc. The amount of crospovidone was larger on the surface of Sample 1 as compared with Sample 2, showing that coating with crospovidone was actually provided by the coating operation described above. In addition, since crospovidone was dispersed throughout the surface of a granule, it was confirmed that coating with crospovidone was homogeneous.

INDUSTRIAL APPLICABILITY

The present invention is utilized for manufacturing of pharmaceutical agents.

The invention claimed is:

1. An intraorally rapidly disintegrating tablet produced by compression of
    a granule, wherein the granule consists of a single coating layer and an inside, and contains no drug; and
    a drug except ambroxol hydrochloride,
    wherein the inside of the granule comprises a disintegrant, and is prepared from a powder comprising the disintegrant, and then the granule is coated with the single coating layer consisting of the disintegrant; and
    wherein preparation of the granule comprises a step of swelling the disintegrant with water and/or ethanol prior to the preparation thereof and a step of drying the granule after coating with the disintegrant.

2. The intraorally rapidly disintegrating tablet according to claim 1, wherein the inside of the granule comprises one or more kinds of pharmaceutically acceptable additives.

3. The intraorally rapidly disintegrating tablet according to claim 1, wherein the granule comprises a void in the inside thereof.

4. The intraorally rapidly disintegrating tablet according to claim 1, wherein the granule inside is prepared from a mixture comprising one or more kinds of pharmaceutically acceptable additives in addition to the disintegrant.

5. The intraorally rapidly disintegrating tablet according to claim 1, wherein the proportion of the disintegrant present in the inside of the granule is 4 to 20% by weight relative to the entire tablet and the proportion of the disintegrant present in the coating of the granule is 4 to 20% by weight relative to the entire tablet.

6. The intraorally rapidly disintegrating tablet according to claim 1, comprising erythritol in the inside of the granule.

7. The intraorally rapidly disintegrating tablet according to claim 6, wherein the proportion of the disintegrant present in the inside of the granule is 4 to 8% by weight relative to an entire tablet and the proportion of the disintegrant present in the coating of the granule is 4 to 8% by weight relative to the entire tablet.

8. The intraorally rapidly disintegrating tablet according to claim 1, comprising mannitol in the inside of the granule.

9. The intraorally rapidly disintegrating tablet according to claim 1, wherein the disintegrant both in the single coating layer and in the inside is crospovidone.

10. The intraorally rapidly disintegrating tablet according to claim 1, wherein the inside of the granule comprises light anhydrous silicic acid or a stearate salt as lubricant.

* * * * *